(12) United States Patent
Snyder (10) Patent No.: US 6,346,654 B1
(45) Date of Patent: Feb. 12, 2002

(54) ARTHROSCOPIC PORTAL DRESSING

(76) Inventor: Stephen J. Snyder, 5055 Amestoy Ave., Encino, CA (US) 91316-3409

( * ) Notice: Subject to any disclaimer, the term of this patent is extended or adjusted under 35 U.S.C. 154(b) by 0 days.

(21) Appl. No.: 09/369,164

(22) Filed: Aug. 5, 1999

(51) Int. Cl.$^7$ ................................................ A61F 13/00
(52) U.S. Cl. ............................ 602/56; 602/41; 602/42; 602/43; 602/57; 602/60
(58) Field of Search ............................... 602/41–59, 75, 602/79, 3; 607/96, 108, 111, 112

(56) References Cited

U.S. PATENT DOCUMENTS

| | | |
|---|---|---|
| 663,749 A | 12/1900 | Gorse |
| 3,463,147 A | 8/1969 | Stubbs |
| 3,490,448 A * | 1/1970 | Grubb ........................ 602/46 |
| 3,521,632 A | 7/1970 | Graham |
| 4,665,909 A * | 5/1987 | Trainor ....................... 602/75 |
| 4,704,107 A | 11/1987 | Coates |
| 4,753,648 A | 6/1988 | Jackson |
| 4,758,241 A | 7/1988 | Papajohn |
| 4,784,128 A | 11/1988 | Scheuermann |
| 5,152,282 A | 10/1992 | Carn et al. |
| 5,425,702 A | 6/1995 | Carn et al. |
| 5,823,977 A * | 10/1998 | Daylea ......................... 602/3 |

* cited by examiner

Primary Examiner—Kim M. Lewis
(74) Attorney, Agent, or Firm—Pandiscio & Pandiscio (57) ABSTRACT

An arthroscopic portal dressing for use as a post operative dressing covering an arthroscopic portal to absorb and conduct away from the patient's skin, collected fluids as are passed out from the portal. The dressing includes an island component that is a pad arranged for fitting over and adhering to the skin surface around the portal to absorb fluids therefrom, and a reservoir cover to fit over one or more portals covered by island components, with the reservoir cover contoured to fit comfortably over a body section, such as a knee or shoulder. Which reservoir cover includes a pad formed from a superabsorbent material, such as a hydrophilic foam, to absorb and contain fluid that has been passed thereto from the island component, and to maintain that collected fluid away from the patient's skin. The reservoir cover includes sides or edges whereto elastic material, such as elastic threads, are secured to draw the reservoir cover's sides or edges into tight fitting engagement over the patient's skin, discouraging fluid leakage from the dressing. The reservoir cover further includes a strap or straps for fitting around the patient's joint to maintain the dressing in place and to apply a constrictive force through the dressing into the incision area to encourage fluid flow from the portal, and, as needed, one or more elastic bands can be fitted around the installed dressing to apply an additional constrictive force to the incision area and to hold a cooling material such as an ice bag or frozen gel material adjacent to the surgical site.

13 Claims, 5 Drawing Sheets

ARTHROSCOPIC PORTAL DRESSING

BACKGROUND OF THE INVENTION

1. Field of the Invention

This invention relates to arthroscopic dressing systems for covering and protecting one or more skin portals which are formed in an arthroscopic surgical procedure and other surgical or medical situations where large volumes of fluid exit the skin openings.

2. Prior Art

Dressings and dressing systems for covering an opening or portal which has been created by puncturing a patient's skin during a surgical procedure have, of course, long been known and are in common use. Such earlier dressing systems used postoperatively to cover the knee or shoulder have, in particular, often been inadequate when the surgical procedure results in considerable fluid drainage. Similarly, dressings for other surgical procedures, such as liposuction, that also involve extensive fluid drainage, have often not been adequate and have required close monitoring to avoid leakage around the dressing. Heretofore, dressings for such procedures have had to be changed often and when such dressings use adhesive tapes to secure the bandage pads in place, such have caused blistering, rashes and pain when removed. Further, such earlier dressings have taken considerable time to maintain, with medical personnel having to regularly check the condition of the dressing.

The invention meets a need for a superabsorbent dressing suitable for holding a large volume of fluid by providing a dressing having, as an absorbent pad component, a mat formed from a highly absorbent material maintained within an elastic edge by adhesive sections to provide a watertight seal, with the selected highly absorbent material providing a wicking action that removes fluid from the wound site and suspends that fluid away from the patient's skin.

Bandages and dressings for fixation to the body and, in particular, to bodily areas at the knee and shoulder are, of course, well known in the art. A very early example of such a dressing for fitting over a specific body area is found in a Gorse, U.S. Pat. No. 663,749, with later dressings designed for convenient application over arm and leg joints shown in Stubbs, U.S. Pat. No. 3,463,147; and Graham, U.S. Pat. No. 3,521,632. None of which earlier dressings, however, provides for sealing the dressing to the patient's skin nor for an island component or components applied first to the skin, with such island component or components constructed of an absorbent material that is capable of efficiently wicking fluid away from the wound site into a second reservoir cover of the dressing.

Examples of a use of highly absorbent materials to absorb and retain body fluids passed from a body cavity are shown in Coates, U.S. Pat. No. 4,704,107; to Jackson, U.S. Pat. No. 4,753,648; and to Papajohn, U.S. Pat. No. 4,758,241. None of which patents, however, deals with surgical dressings. Surgical dressings having an absorbent pad that is sealed by a separate section of material whereto an adhesive is applied are shown in Scheuermann, U.S. Pat. No. 4,784,128; to Carn, et al., U.S. Pat. No. 5,425,702; and to Carn, et al., U.S. Pat. No. 5,152,282. However, none of these dressings involves separate components, like the invention, to include one or more island components that are placed over a portal formed through a patient's skin, which island component or components are then covered by a reservoir component that is an absorbent pad placed over the island component or components. Unique to the invention, the island component or components are fitted and maintained over the portal and may or may not include an adhesive outer rim. Also, the reservoir cover, designed to fit over the installed island component or components and surrounding skin, is an absorbent pad that collects and holds fluids which have passed though the island component or components and gently compresses the surgical field to encourage fluid to egress through the portal, decreasing swelling of the extremity. The reservoir cover that is placed over the island component or components collects and holds the postoperative drainage fluid and prevents fluid escape during the postoperative period.

SUMMARY OF THE INVENTION

It is a principal object of the present invention in an arthroscopic portal dressing to provide a surgical dressing that is composed of separate dressing components to include an island component or components that are placed over an arthroscopic portal to capture and hold fluids, causing the fluids to drain away from the portal and away from the patient's skin, and a separate reservoir cover component that is provided to cover the island component or components and surrounding skin area to collect and hold fluids passing through the island component or components, holding such collected fluids over a significant period of time.

Another object of the present invention in an arthroscopic portal dressing is to provide, as an island component, a highly absorbent pad that is secured, in sealing engagement, to the patient's skin around the portal to absorb and wick away collected fluid passed from that portal, and a reservoir cover that also includes a highly adsorbent but larger pad that is covered with a water impervious material, with the pad to receive and contain fluid passed thereto from the island component or components and with the reservoir cover having edges that are contoured and formed to fit closely to the area of the skin contacted by the cover edges.

Another object of the present invention in an arthroscopic portal dressing is to provide, with the reservoir cover, a dressing that conforms to the contours of a body area, such as the knee or shoulder, and is arranged to fit closely and maintain the cover edges to the skin surface.

Still another object of the present invention in an arthroscopic portal dressing is to provide an arrangement for gently compressing the skin and soft tissues at the portal to encourage drainage.

Still another object of the present invention in an arthroscopic portal dressing is to provide a dressing consisting of an island component or components that are formed from an absorbent pad material and are each arranged for seating over a portal to seal around the pad edges with the material selected for the pad to wick fluids passed from the portal away from the skin surface; and a reservoir cover that also includes an absorbent pad and is maintained by a waterproof cover over the island component or components to collect and maintain fluid passed from the island component or components away from the patient's skin for a significant period of time.

Still anther object of the present invention in an arthroscopic portal dressing is to provide a dressing that is easy and convenient to apply to a patient's incision portal to contain a large volume of fluid passed from the portal and to discourage fluid leakage from the dressing edges over a significant period of time between dressing changes.

The arthroscopic portal dressing of the invention includes separate components that are individually arranged for convenient application over an arthroscopic portal or portals that has or have been formed into a patient's skin, as for example during a knee or shoulder surgery, and wherefrom bodily fluids drain. The dressing includes an island component that includes a pad formed from a highly absorbent material, such as a hydrophilic foam, that is surrounded by an adhesive rim or coated border that, when pressed onto the skin area surrounding the portal, will seal thereto, with the pad to wick bodily fluids from the portal away from the skin. The dressing further includes a reservoir cover that also incorporates an absorbent pad covered by a section of a water impervious material and is contoured to fit over the skin area around the portal. For example, where the dressing is used to cover a knee portal or portals as formed in a knee arthroscopic surgical procedure, the cover may be formed as a trapezoid with the long side to be fitted around the thigh and the short side to fit around the leg. Where, when such dressing is to be applied to cover a shoulder portal or portals, the cover can be formed to have a butterfly shape having pairs of wings of different lengths. The pair of wings having the longer lengths are to extend across the collar area with the shorter length wings to join around the arm. To maintain the reservoir cover in place, so as to hold the fluid absorbent pad material onto the patient's skin, covering over the island portal or portals, the opposite reservoir cover ends may be bound with a thin section of a waterproof material and may include an elastic material, such as an elastic thread that is sewn along the cover ends and is used to draw the cover ends closely to the skin surface, sealing against fluid passage. Further, a strap or straps are provided with the cover to wrap around the dressing, providing a tight or constricted fit of the reservoir cover over the portal or portals in the skin, encouraging a fluid flow therefrom and may be used to hold a cold, gel, or ice pack, or the like, over the joint. Alternatively, to further increase compression to the area around the portal or portals, an elastic band can be fitted around the dressing. Also, depending upon the dressing use, the reservoir cover edges can include a strip or strips of a skin friendly adhesive, or velcro type fastening strips which can be secured thereto, for coupling to one another to secure the reservoir cover over the island component or components and surrounding skin surface area, as appropriate.

BRIEF DESCRIPTION OF THE DRAWINGS

These and other objects and features of the present invention in an arthroscopic portal dressing will become more fully apparent from the following description in which the invention is described in detail in conjunction with the accompanying drawings.

DETAILED DESCRIPTION

In performing an arthroscopic surgical procedure at least one and usually several ports or portals are formed through a patient's skin and into a joint area, such as his shoulder or knee. Such portals are left open to drain after such procedure, often producing a considerable volume of fluid. This is likewise true in other surgical procedures, such as liposuction, for which the dressing of the invention can be used on. For the present disclosure, dressings for covering portals formed during knee and shoulder arthroscopic surgical procedures are shown and should be understood to be the best modes currently contemplated for using the invention. It should, however, be understood that the invention is not limited to the embodiments shown, and can be practiced on differently configured dressings that embody the structural elements of the dressings as shown and described herein, within the scope of this disclosure.

Figure 1:
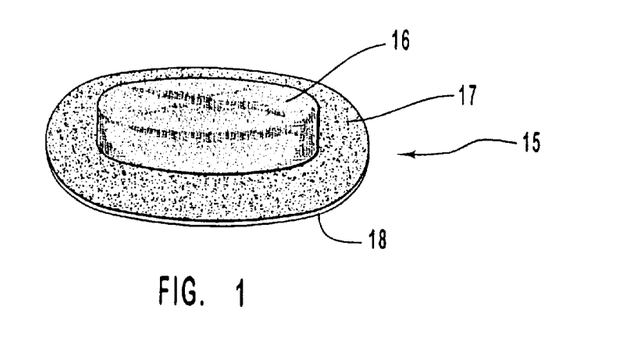
FIG. 1 is a frontal perspective view of an elliptically shaped island component of an arthroscopic portal dressing of the invention.
Figures 8, 9:
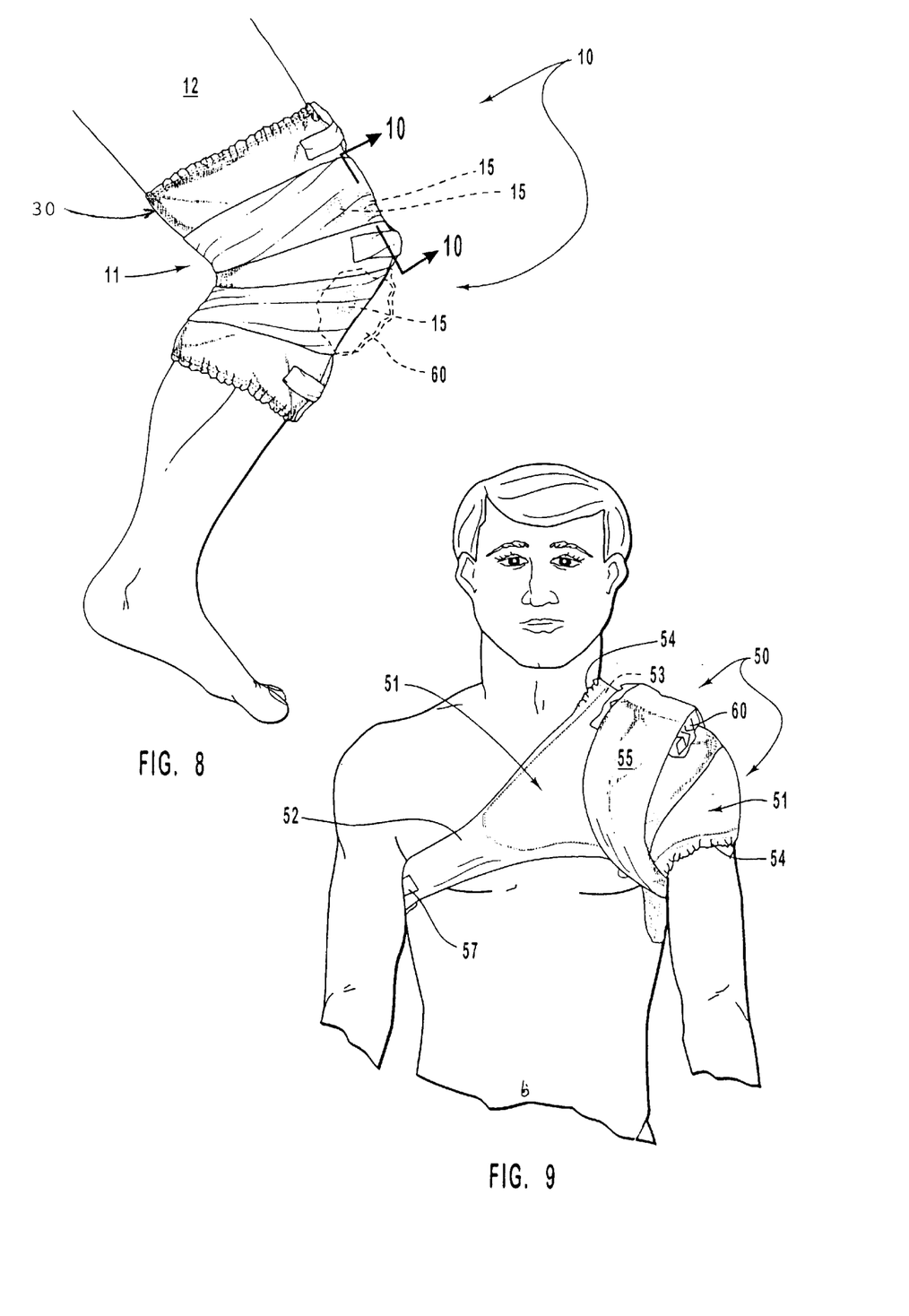
FIG. 8 is a side elevation view of the patient's knee of FIG. 4 shown as having the reservoir cover of FIG. 6 fitted thereto with the island components of FIG. 1 shown in broken lines.
FIG. 9 is a front elevation view of the patient's head and torso of FIG. 5 with his left shoulder shown as having the reservoir cover of FIG. 7 fitted thereto.
Figure 10:
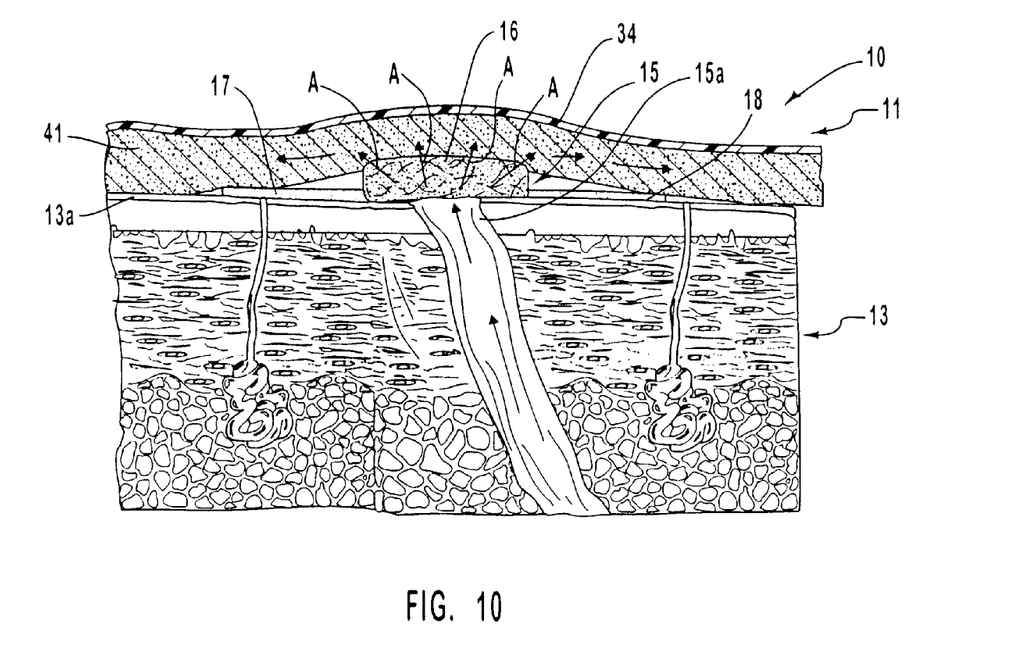
FIG. 10 is an enlarged sectional view taken along the line 10—10 of FIG. 8 showing a cross section of the reservoir cover positioned over an elliptical island component of FIG. 1 maintained to the patient's skin above a portal that has been formed through layers of the patient's skin, above the knee joint and showing, with arrows A, a fluid flow path from the portal through the island component and into the absorbent material pad of the reservoir cover.

FIG. 8 shows a knee embodiment of the arthroscopic portal dressing of the invention 10, that includes a reservoir cover 11 that is shown wrapped around a knee 13 (FIG. 4) of a patient's leg 12 and, as shown in broken lines, covers an elliptical shaped island component 15 of the invention, as shown in FIG. 1. Each island component 15 is maintained in covering arrangement over a portal or portals formed in knee 13 of FIG. 4, and over a portal or portals formed in shoulder 14 of FIG. 5. The island component 15 is shown in an enlarged sectional view in FIG. 10 covering over a portal 15a that is formed into knee 13. The island component 15, as shown in FIG. 1, includes a pad 16 that is formed as a flat ellipse and is preferably between approximately one (1) to five (5) millimeters high, and is formed from a material that is a superabsorbent, such as a hydrophilic foam. Though, it should be understood, another like material could be so used within the scope of this disclosure. The hydrophilic foam pad is designed to rapidly absorb liquid as it flows out from the portal and to channel the flow into the pad 41, (FIG. 10)

with the pad wicking the fluid away from the skin. The hydrophilic foam pad will ultimately pass that fluid therethrough and into an overlying reservoir cover, as set out below.

Figure 2:
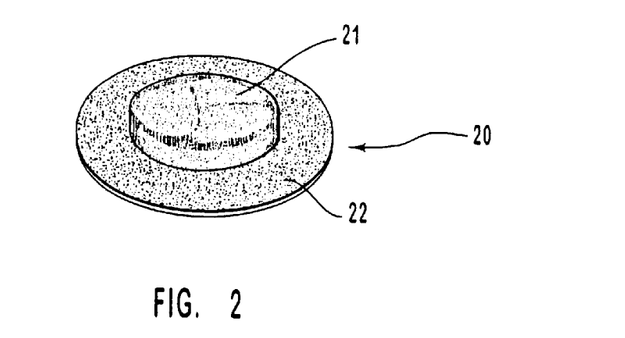
FIG. 2 is a view like that of FIG. 1 only showing a round rather than elliptically shaped island component.
Figure 3:
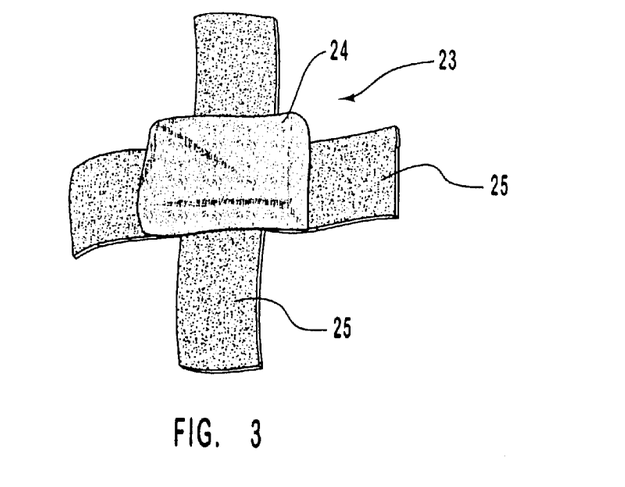
FIG. 3 is a view like that of FIG. I only showing the island component as an absorbent pad mounted to a center of crossed adhesive strips.

The pad 16, and pads 21 and 24 of the island components 20 and 23 of FIGS. 2 and 3, respectively, may be used alone by applying a layer of an adhesive, that is preferably a skin friendly adhesive, onto an under surface thereof. Within the scope of this disclosure, however, a flat wide rim 17, as shown in FIG. 1, is preferably secured to a lower outer edge of the pad 16. The flat wide rim 17 is similar to a common toe corn pad and includes a skin friendly adhesive on its undersurface that is to be pressed against the skin 13a, as shown in FIG. 10. The island component 15 is thereby maintained over arthroscopic portal 15a.

FIGS. 2 and 3, respectively, show two additional embodiments of island components, herein identified as island components 20 and 25. It should, however, be understood, that the island component of the invention is not limited to the configurations shown in FIGS. 1 through 3, and can include other appropriate shapes, such as a triangle, rectangle, square, trapezoid, or the like, within the scope of this disclosure.

Island component 20, as shown in FIG. 2, has a thin round pad section 21, that is also preferably formed from a superabsorbent material, specifically the material utilized for island component 15. Accordingly, island component 20 is like and is intended to function like island component 15, and preferably includes an outer flat rim 22 whereto a skin friendly adhesive is applied to the rim's lower surface enabling it to stick onto a patient's skin. Similarly, in FIG. 3 is shown another island component 23 that includes a flat rectangular pad 24 that, it should be understood, is preferably formed from a superabsorbent material like that described for use with island component 15. The island component 23 includes crossed adhesive tape strips 25 that, like the flat wide rim 17 of island component 15, are open across the undersurface, exposing the pad 24 undersurface to the portal opening. The island component 23 is arranged to be applied and function like the island components 15 and 20, as described above and as set out herein below.

Figure 4:
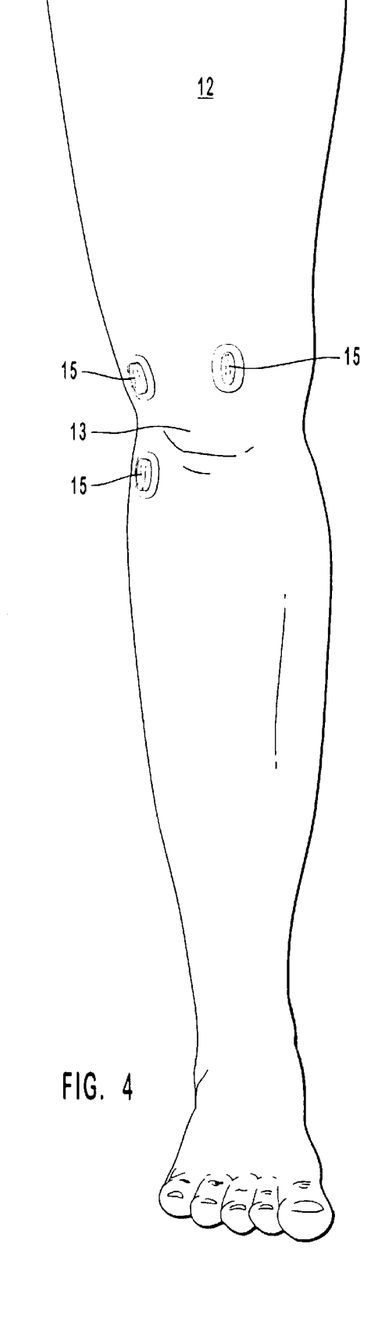
FIG. 4 is a front elevation of a patient's knee showing elliptical island components of FIG. 1 applied over each of three arthroscopic portals.
Figure 5:
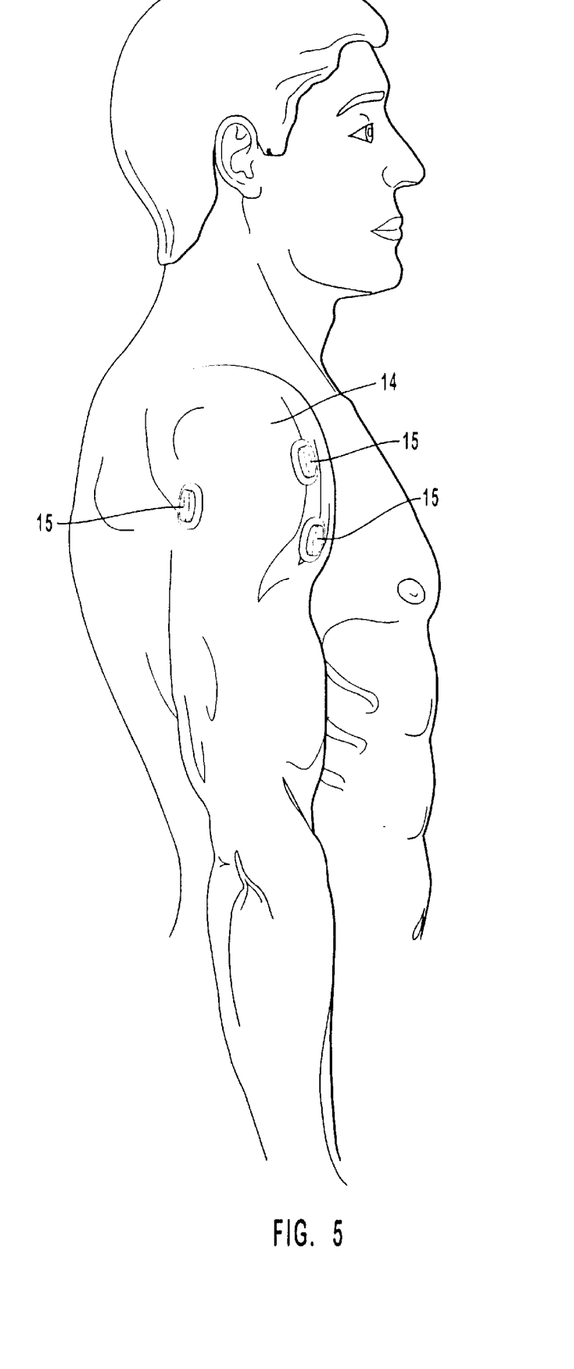
FIG. 5 is a side elevation view of a patient's torso, head and shoulder areas, showing elliptical island components of FIG. 1 applied over each of three arthroscopic portals formed in the patient's shoulder.

FIGS. 4 and 5 show, respectively, a patient's leg 12 and knee 13, and the patient's shoulder 14, with both the knee 13 and shoulder 14 shown as having had island components 15 applied over arthroscopic surgical portals formed therein. In FIG. 8, the knee 13 with the island components 15 applied thereto is shown as having been wrapped with reservoir cover 11, which cover is shown removed and enlarged in FIG. 6, the island components 15 and reservoir cover 11 forming the arthroscopic portal dressing 10. Shown in FIGS. 6 and 8, the reservoir cover 11 is preferably formed as a flat trapezoidal shaped section 30 for application around the knee 13, where the wide or long trapezoid side 31 is fitted around the thigh, and the shorter trapezoid side 31a is wrapped around the upper calf, as shown in FIG. 8. In that wrapping, straps 32, that are each secured at one end 33 onto the cover's outer layer 34, are passed over the knee cap and connect onto the cover at their opposite ends 35 to hold the cover tightly around the knee as shown. The opposite strap ends 35, preferably including VELCRO-type (e.g., hook and loop) mats 36 fixed thereto, that are pressed together connecting ends 35 onto the cover top surface 34, as shown in FIG. 8. So arranged, the straps 32 serve to both maintain the reservoir cover around the knee 13, holding it in position over the island components 15, and with the straps further serving to apply compression to the body area under the portals to encourage fluid drainage from each portal opening 15a, as shown in FIG. 10. Additionally, for maintaining the reservoir cover 11 around the knee, ends of adhesive strips 38, shown in FIG. 6, are secured at spaced intervals to one cover edge 39 and are to be pulled across the other cover edge 40, as shown in FIG. 8, to maintain the one cover edge 39 over the other.

Figure 6:
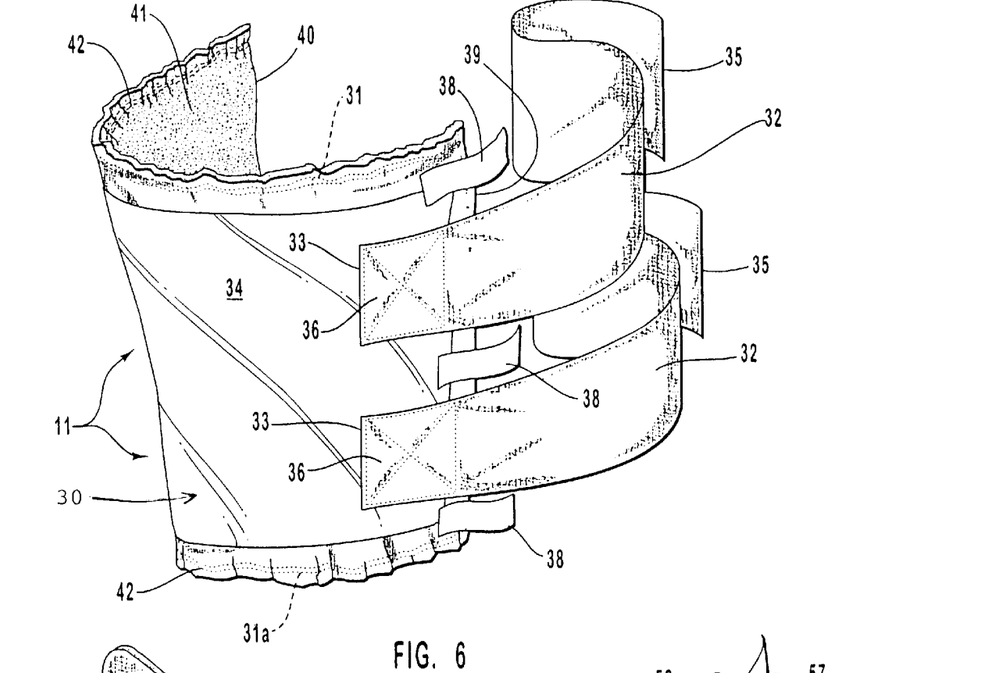
FIG. 6 is a frontal elevation perspective view of a reservoir cover of the invention, shown as having a trapezoidal shape, to fit, as shown in FIG. 8, around a patient's knee, and including a reservoir pad that is formed from a hydrophilic material and is maintained by an outer waterproof covering and further includes spaced constriction bands that are secured at their ends to extend from one covering edge to be passed around the patient's knee and secured together at their other ends, as with velcro type fasteners.

The reservoir cover 11, as shown in FIG. 6, includes the outer layer 34, that is a sheet of fluid impervious flexible material, preferably a thin sheet of a plastic material such as a Vidrape. A pad of a superabsorbent material 41 is secured as by adhesive bonding to the undersurface of the outer layer 34. The pad of absorbent material 41 is preferably a hydrophilic foam or other superabsorbent material, and the foam described above for use as pads 16, 21 and 24, can be used for this purpose. The pad of material 41, as shown in FIG. 10, receives a fluid flow as is passed up through each island component 15 pad, shown as arrows A in FIG. 10, and is distributed throughout the pad of material 41, with the pad of material 41 maintaining the collected fluid away from the patent's skin.

The reservoir cover 11 absorbs fluid as it passes from each island component 15 and discourages fluid leakage past the outside cover 11. The top and bottom sides 31 and 31a, respectively, are fitted with an elastic material at the perimeter area of each side that pulls the side tightly against the patient's skin. The elasticity, as shown in FIG. 6, is provided by an elastic thread 42 that is sewn through both the outer layer 34 and the pad of absorbent material 41. Additionally, to further hold the reservoir cover in place and provide for compression of the portal, a band or bands 32, that are preferably formed from an elastic material, is separately installed, as shown in FIG. 6, around the arthroscopic portal dressing 10, as needed, to encourage a fluid flow out from the portal.

FIG. 9 shows another embodiment 50 of an arthroscopic portal dressing 10 that also utilizes at least one island component covering portals as have been formed into the patient's shoulder 14, as shown in FIG. 5. Further, additional to island component or components, the dressing 50 includes a reservoir cover 51 that is formed from a section of a flexible water impervious material 52 having a pad 53 secured to an undersurface thereof, which pad 53 is formed from a thin section of a superabsorbent material. The dressing's reservoir cover 51 is preferably a thin section of a flexible water impervious material 52 having a butterfly shape, whereto the absorbent pad 53, as shown in broken lines, is secured to the undersurface thereof, covering a center area. The pad 53, like the pad 41, is preferably formed as a thin section of a superabsorbent material, such as a hydrophilic foam material, like that set out above, and is provided to absorb and hold fluid as it passes through the island component, as shown in FIG. 10.

Figure 7:
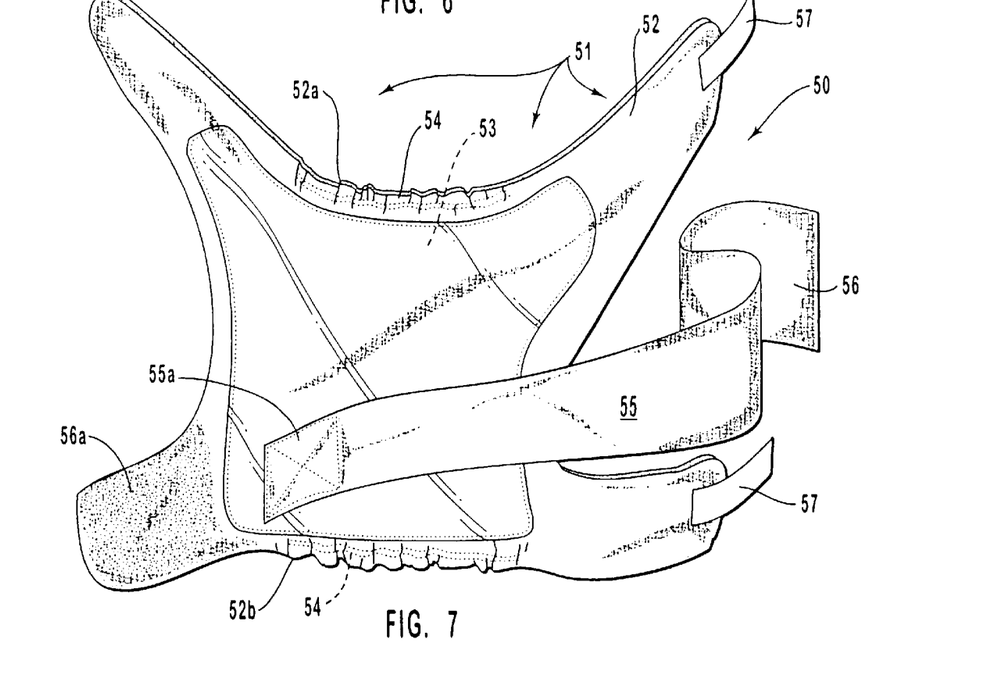
FIG. 7 is a frontal elevation perspective view like FIG. 6 only showing a reservoir cover that is formed to have a butterfly shape with pairs of longer and shorter wing sections, respectively, extending outwardly from across a longitudinal center axis, the longer top wing sections to fit across the patient's collar area with the shorter wing sections to fit around the patient's arm, as shown in FIG. 9, and including a single constriction band to be fitted under the patient's arm.

Shown in FIG. 7, the reservoir cover material 52 includes elastic side sections, that, like the elastic sections 31 and 31a of reservoir cover 11, are formed by sewing an elastic thread 54, shown in broken lines, along the top and bottom end portions 52a and 52b, respectively, of the outer cover surface. So arranged, the outer cover top and bottom end sections 52a and 52b are urged into close contact with the patient's skin, discouraging fluid flow out from beneath the dressing around the patient's arm and neck. Like the reservoir cover 11, the reservoir cover 51 also includes a strap 55 secured at its one end 55a onto the flexible outer cover 51 top surface to be passed, as shown in FIG. 9, under the patient's arm pit to where an opposite fastening strap end 56 engages and connects to a coupling pad 56a that is formed onto the top surface of the flexible outer cover 51, at a butterfly short wing end, as shown in FIG. 9. So arranged, the elastic thread sewn into end sections 52a and 52b will hold the dressing in place and, as needed, will add compression at the incision site. Additionally, for maintaining the reservoir cover 51 over the island component or components, strips of adhesive tape 57 are preferably provided to aligned butterfly wing ends, as shown in FIG. 9, which strips of tape 57 are to stick to the wing of the opposite side further holding the dressing in place.

In practice, the embodiments of the arthroscopic portal dressing 10 each provide, as illustrated in FIG. 10, for covering a skin portal 15a which has first been covered by an island component 15, fitted thereto. The island component seals over the portal opening and captures fluid flowing from that portal, as shown as arrows A. Such fluid is absorbed into the pad 16, passes therethrough into the pad 41 of the reservoir cover 11 that is maintained over the island component and over a surrounding area of the patient's skin by the waterproof cover 34. So arranged the fluid flow will be contained in pad 41 for a significant period of time between dressing changes. To discourage fluid flow out from under the cover 34 edges, the cover has elastic thread for reinforcement along its edges which pulls the edges into close contact with the patient's skin. Further, a strap or straps are provided to wrap around the reservoir cover 11, securing it in place, and providing, as needed, a compressive force at the incision site, to encourage fluid drainage out from the portal. The compressive force can be augmented, as needed, by fitting the elastic band or strap 55 around the dressing. This strap can also be used to maintain an ice pack 60, shown in broken lines in FIG. 8 and shown as held in place by the elastic strap in FIG. 9.

Preferred embodiments of the present invention in an arthroscopic portal dressing have been shown and described herein. It should, however, be apparent that this disclosure is made by way of example only, and that variations and modifications to the arthroscopic portal dressing of the invention are possible, within the scope of this disclosure, without departing from the subject matter coming within the scope of the following claims and a reasonable equivalency thereof, which claims I regard as my invention.

What is claimed is:

1. An arthroscopic portal dressing comprising:

a wicking component for positioning against an arthroscopic portal following surgery and for receiving fluid from the arthroscopic portal as fluid drains from the arthroscopic portal and for wicking that fluid away from the arthroscopic portal; and a reservoir component for overlying the wicking component and for receiving fluid from the wicking component and for storing and containing the fluid;

said wicking component comprising a wick element and an adhesive element, said wick element comprising a wicking material having an inner surface for positioning against the arthroscopic portal and an outer surface for engagement with said reservoir component, and said adhesive element of said wicking component being attached to said wick element and adapted to hold said wick element against the skin of the patient without significantly restricting the capacity of said wick component to pass fluid to said reservoir component; and said reservoir component comprising a reservoir element, a waterproof element and an adhesive element, said reservoir element comprising an absorbent material having an inner surface for engagement with said wicking component and an outer surface for engagement with said waterproof element, and said adhesive element being attached to said waterproof element and adapted to hold said reservoir element against said wicking component so that fluid will be transferred from said wick element to said reservoir element and to hold said waterproof element against the skin of the patient, whereby to contain fluid held in said reservoir element.

2. An arthroscopic portal dressing as recited in claim 1, wherein the wicking component's wick element is formed of a hydrophilic foam material and fits over the portal as a flat section having a height of approximately two (2) to ten (10) millimeters.

3. An arthroscopic portal dressing as recited in claim 1, wherein the wicking component's adhesive element comprises a layer of an adhesive applied to the undersurface of the wicking component's wick element that adheres to the patient's skin around the portal.

4. An arthroscopic portal dressing as recited in claim 1, wherein wicking component's adhesive element comprises an outer border secured around the base of the wicking component's wick element that includes an adhesive means for attachment onto the patient's skin around the portal.

5. An arthroscopic portal dressing as recited in claim 1, wherein the wicking component's adhesive element comprises a pair of crossed adhesive strips that are open at their centers to pass fluid therethrough into the wicking component's wick element.

6. An arthroscopic portal dressing as recited in claim 1, wherein the reservoir component's waterproof section is formed from a sheet of a flexible plastic material that has the reservoir element bonded to an undersurface thereof.

7. An arthroscopic portal dressing as recited in claim 6, wherein the reservoir element is formed from a hydrophilic foam or other superabsorbent material and has a thickness of from ten (10) to fifty (50) millimeters.

8. An arthroscopic portal dressing as recited in claim 1, wherein one end of at least one strap is secured to the reservoir component's waterproof element to pass around the patient's body, with the other end of said strap arranged to be releasably fixed back to the reservoir component's waterproof element.

9. An arthroscopic portal dressing as recited in claim 8, further including at least one adhesive tape or VELCRO (hook and look) strip having one end thereof secured to a top surface of the reservoir component's waterproof element, with said adhesive tape or VELCRO (hook and look) strip to extend therefrom and stick to a surface of said reservoir component's waterproof element or to a patient's skin.

10. An arthroscopic portal dressing as recited in claim 8, wherein the reservoir component's waterproof element has a trapezoid shape, with a long side of said trapezoid to be fitted around the patient's thigh, above his knee, and with the opposite short side of said trapezoid to be fitted around the patient's leg, below his knee; and each said trapezoid long and short side includes an elastic means fitted thereto to provide for drawing each said side into a close fitting engagement with the patient's skin.

11. An arthroscopic portal dressing as recited in claim 8, wherein the reservoir component's waterproof element has a butterfly shape with pairs of long and short wing sections, respectively, extending outwardly from a longitudinal center axis, with said wing sections each having a length, where said long wing sections will fit across the patient's collar area and said short wing sections will connect around the patient's arm; and elastic means fitted to the edges of the reservoir component's waterproof element between, respectively, said long wing sections and said short wing sections, for drawing each said edge into a close fitting engagement to patient's skin.

12. An arthroscopic portal dressing as recited in claim 1, further including at least one elastic band means for fitting around the dressing to apply a compressive force to the area of the patient's skin wherein the portal is formed or for securing an ice bag for cooling the surgical site.

13. A method for collecting and storing fluid draining from an arthroscopic portal following surgery, said method comprising the steps of:

providing a wicking component comprising a wick element, and providing a reservoir component for receiving fluid from the wicking component and for storing and containing the fluid, said reservoir component comprising a reservoir element and a waterproof element;

positioning the wicking component against an arthroscopic portal following surgery so that the wick element receives fluid from the arthroscopic portal and wicks the fluid away from the arthroscopic portal; and positioning the reservoir component over the wicking component so that the reservoir element receives fluid from the wick element and stores the same, with the waterproof element containing the fluid in the reservoir element.

* * * * *